United States Patent [19]
Guerry et al.

[11] Patent Number: 5,494,795
[45] Date of Patent: Feb. 27, 1996

[54] SPECIFIC OLIGONUCLEOTIDE PRIMERS FOR DETECTION OF PATHOGENIC CAMPYLOBACTER BACTERIA BY POLYMERASE CHAIN REACTION

[75] Inventors: Patricia Guerry, Rockville, Md.; Trevor J. Trust, Victoria, Canada

[73] Assignee: The United States as represented by the Secretary of the Navy, Washington, D.C.

[21] Appl. No.: 56,538

[22] Filed: May 5, 1993

[51] Int. Cl.⁶ .............................. C12Q 1/68; C12P 19/34; C07H 21/04
[52] U.S. Cl. .................. 435/6; 435/91.2; 536/24.32; 536/24.33; 536/23.7; 935/77; 935/78; 935/8; 514/44
[58] Field of Search ................... 536/23.7, 24.32, 536/24.33; 435/91, 6, 91.2; 935/78; 514/44

[56] References Cited

PUBLICATIONS

Eisenstein, The New England Journal of Medicine, Jan. 18, 1990, pp. 178–183.
Guerry et al., J. Bact., 172(4), Apr. 1990, pp. 1853–1860.
J. Clin Microbiology, (Oct. 1992), 30:2613–2619, Oyofo et al.
Guerry et al., Campylobacter Jejuni: Current Status and Future Trends, Ch. 30, 1992, pp. 267–281.
Logan et al., J. Bacteriol., vol. 171, No. 6, Jun. 1989, pp. 3031–3038.
Thornton et al., Infect. Immun., vol., 58, No. 8, Aug. 1990, pp. 2686–2689.
Guerry et al., J. Bacteriol., vol. 173, No. 15, Aug. 1991, pp. 4757–4764.

*Primary Examiner*—Stephanie W. Zitomer
*Assistant Examiner*—Carla Myers
*Attorney, Agent, or Firm*—A. David Spevack; William C. Garvert

[57] ABSTRACT

This invention is a specific set of oligonucleotide PCR primers (pg50 and pg3) and a specific oligonucleotide probe (pBA273) for detection of PCR-amplified DNA from pathogenic strains of Campylobacter, specifically *C. coli* and *C. jejuni*, in fecal specimens.

6 Claims, 1 Drawing Sheet

SPECIFIC OLIGONUCLEOTIDE PRIMERS FOR DETECTION OF PATHOGENIC CAMPYLOBACTER BACTERIA BY POLYMERASE CHAIN REACTION

BACKGROUND OF THE INVENTION

1. Field of the Invention

This invention relates to a method for detection of pathogenic Campylobacter bacteria using specific oligonucleotide primers for amplification of DNA sequences by polymerase chain reaction.

2. Description of the Prior Art

Certain thermophilic Campylobacter species, particularly *C. jejuni* and *C. coli*, are among the most frequently isolated bacteria causing diarrheal disease in humans (I. Nachamkin, et al., "*Campylobacter jejuni:* Current Status and Future Trends," Amer. Soc. Microbiol., Washington, D.C., 1991, pp 9–19, 20–30). Their reliable detection by conventional culture techniques is made difficult by their susceptibility to oxygen toxicity during transport, slow rate of growth and fastidious growth requirements. An improved method is needed for detection of these important human pathogens.

The polymerase chain reaction (PCR) has been applied extensively to the detection of infectious agents (B. I. Eisenstein, New Engl. J. Med. 322:178–183, 1990). PCR allows amplification of a preselected region of DNA and can serve as a highly specific and sensitive detection method (K. B. Mullis and F. A. Faloona, Methods Enzymol. 155:335–350, 1987). PCR can also be used for the direct identification of organisms in complex substrates without prior isolation and purification of the organism (D. M. Olive, J. Clin. Microbiol. 27:261–265, 1989). Unique genetic characteristics of the Campylobacter relative to other intestinal bacteria (P. J. Romaniuk, et at., J. Bacteriol. 170:2137–2141, 1987) make them suitable candidates for detection by PCR. The prior references do not teach effective or suitable primers.

SUMMARY OF THE INVENTION

Accordingly, an object of this invention is a set of oligonucleotide primers (termed pg50 [sequence 5'-ATGGGATTTCGTATTAAC-3'(SEQ ID No. 1)] and pg3 [sequence 5'-GAACTTGAACCGATTTG-3'](SEQ ID No. 2) for PCR amplification of Campylobacter DNA gene sequences, and a labeled 273-base pair DNA probe (termed pBA273) for detection through hybridization of the PCR-amplified DNA, that detects DNA from pathogenic species of Campylobacter bacteria.

An additional object of this invention is the demonstration of the specificity of the above oligonucleotide primers and probe combination for detection of *Campylobacter coli* and *Campylobacter jejuni* but not other intestinal microorganisms.

An additional object of this invention is the demonstration that the combined use of the above oligonucleotide primers and the above probe are capable of detecting both *C. coli* and *C. jejuni* in fecal specimens with a sensitivity of 30 to 60 bacteria.

These and additional objects of the invention are accomplished by application of standard PCR methodology employing the oligonucleotide primers pg50 (5'-ATGGGATTTCGTATTAAC-3'(SEQ ID No. 1)) and pg3 (5'-GAACTTGAACCGATTTG-3'(SEQ ID No. 2)) to amplify DNA from the flaA flagellin gene of *Campylobacter coli* strain VC167 and the digoxigenin-labeled probe pBA273 to detect the amplified DNA in fecal specimens (extracted by the method of G. Frankel, et al., Mol. Microbiol. 3:1729–1734, 1989) of animals and humans.

BRIEF DESCRIPTION OF THE DRAWINGS

A more complete appreciation of the invention will be readily obtained by reference to the following Description of the Preferred Embodiments and the accompanying drawing. The representations in the figure are diagrammatic and no attempt is made to indicate actual scales or precise ratios. Proportional relationships are shown as approximations.

DESCRIPTION OF THE PREFERRED EMBODIMENTS

Figure 1:
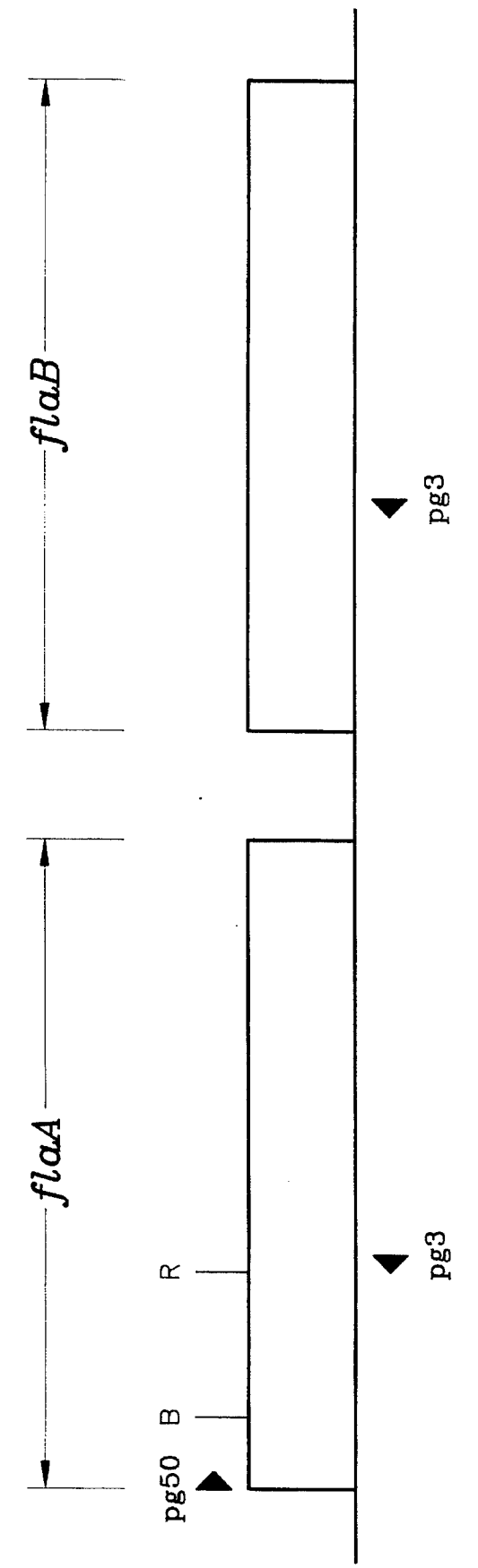
FIG. 1 is a schematic representation of the two flagellin genes of *C. coli* VC167. The binding positions of primers pg50 and pg3 are indicated. Restriction sites are as follows: B, BglII; R, EcoRI. The region between these two restriction sites represents the 273-base pair fragment present in the probe pBA273.

The preferred embodiment of this invention is a specific set of oligonucleotide PCR primers (pg50 [Seq.ID No. 1] and pg3 [Seq.ID No. 2]) and a specific DNA probe (pBA273) for detection of PCR-amplified DNA from pathogenic strains of Campylobacter, specifically *C. coli* and *C. jejuni*, in fecal specimens. Any oligonucleotide or DNA probe may be used that is internal to the sequence amplified by PCR primers pg50 and pg3. The label can be any one of the art recognized labels commonly used in DNA blotting.

One Campylobacter gene that has the potential to allow for organism identification at the level of species and at the narrower level of strain is the flagellin gene. Flagella are extracellular structures used for locomotion by bacteria. The flagella of *C. jejuni* and *C. coli* are composed of two cloned subunit flagellin proteins, the products of the flaA and flaB genes (P. Guerry, et at., J. Bacteriol. 172:1853–1860, 1990). These genes contain highly variable regions that can potentially be used for strain-specific detection and other regions that are highly conserved among *C. coli* and *C. jejuni* strains (S. A. Thornton, et al., Infect. Immun. 58:2686–2689, 1990).

Two oligonucleotides, pg50 (5'-ATGGGATTTCGTATTAAC-3'(SEQ ID No. 1)) and pg3 ( 5'-GAACTTGAACCGATTTG-3'(SEQ ID No 2)), have been selected from the DNA sequence of the flaA flagellin gene (base pairs 289–2007, GenBank Accession No. M64670) of *C. coli* strain VC167 (see FIG. 1); pg50 is between base pairs 289–306 and pg3 is between base pairs 730–746 on the minus strand. These two oligonucleotides function as specific primers for PCR amplification of *C. coli* and *C. jejuni* DNA. A probe internal to the amplified gene region was constructed by standard methods (T. Maniatis, et al., Molecular Cloning: A Laboratory Manual. Cold Spring Harbor Lab., Cold Spring Harbor, N.Y., 1982) for detection of the PCR-amplified Campylobacter DNA. The probe lies between base pairs 481–759 of the DNA in GenBank Accession No. M64670. The results were reported by poster presentation at the American Society for Microbiology on 30 May 1992 (Abstracts of the General Meeting, D-206, p. 130) and in the J. Clin. Microbiol. 30:2613–2619, 1992, by the inventors, and are described in detail below.

Having described the invention, the following examples are given to illustrate specific applications of the invention including the best mode now known to perform the invention. These specific examples are not intended to limit the scope of the invention described in this application.

EXAMPLE

Bacterial Strains and Growth Conditions

All bacterial strains used in this study and their sources are listed in Table 1. Campylobacter and Helicobacter spp. were grown on Mueller-Hinton medium in an atmosphere of 10% $CO_2$-5% $O_2$-85% $N_2$ at 37° C. Members of the family Enterobacteriaceae were grown on Luria agar (T. Maniatis, et al., Molecular Cloning: A Laboratory Manual. Cold Spring Harbor Lab., Cold Spring Harbor, N.Y., 1982). Other bacteria were grown on blood agar plates (Remel, Lenexa, Kans.) and were incubated under normal atmospheric conditions (with the exception of the anaerobe *Wolinella recta*) at 37° C.

DNA Extractions

DNA extractions for the PCR assay were done by three different protocols. Purified DNA from Campylobacter spp. was prepared as described by Logan, et al. (J. Bacteriol. 171:3031–3038, 1989). Two different protocols for extraction of crude DNA from bacterial cultures were used: the phenol-chloroform extraction method of Frankel et al. (Mol. Microbiol. 3:1729–1734, 1989) and the boiling method of van Eys et al. (J. Clin. Microbiol. 27:2258–2262, 1989). Extraction of DNA from rectal swab specimens from rabbits was also performed by the method of Frankel et al. (ibid). Plasmid DNAs were isolated by the method of Birnboim and Doly (Nucl. Acids Res. 7:513–1523, 1979).

Selection of the PCR Primers

The oligonucleotide primers pg50 ( 5'-ATGGGATTTCG-TATTAAC-3'(SEQ ID No. 1)) and pg3 (5'-GAACT-TGAACCGATTTG-3'(SEQ ID No. 2)) derived from the well-conserved amino terminus of the flaA flagellin gene of *Campylobacter coli* strain VC167 (P. Guerry, et al., J. Bacteriol. 172:1853–1860, 1990; cf. FIG. 1) were selected following comparison of 30 strains of *C. coli* and *C. jejuni* by DNA hybridization (S. A. Thornton., et al., Infect. Immun. 58:2686–2698, 1990) and N-terminal amino acid sequencing of flagella from various strains of *C. coli* and *C. jejuni*. These oligonucleotide sequences represent well-conserved but distinctive DNA sequences in the flaA N-termini of both *C. coli* and *C. jejuni* but are not present in DNA sequences of other Campylobacter spp. such J. Clinical Microbiology 1992). Primer pg50 binds to the beginning of flaA but not flaB; primer pg3 binds to the second strand 450 base pairs downstream from the pg50-binding site on flaA as well as at the corresponding position of flaB.

PCR Amplification pg50 and pg3 oligonucleotides were synthesized commercially (Synthecell, Gaithersburg, Md.). The amplification reaction was performed in a volume of 100 μL containing 0.13 to 1.0 μg of sample DNA; 10 mM Tris-HCl (pH 8.3); 50 mM KCl; 1.5 mM $MgCl_2$; 0.01% gelatin; 200 μM (each) dATP, dCTP, dTTP, and dGTP; 200 ng of each primer; and 2.5 U of AmpliTaq DNA polymerase (Perkin-Elmer Cetus). Parameters for the amplification cycles were denaturation for 1 min at 94° C., annealing of primers for 1 min at 37° C., and primer extension for 1 min at 72° C. When VC167 DNA is used in this assay, the primers generate a primary DNA product that runs at the predicted 450 base pair size upon electrophoresis in 2% agarose and that hybridizes to a full-length flagellin gene probe from plasmid pGK213 (P. Guerry, et al., J. Bacteriol. 173:4757–4764, 1991) as well as the pBA273 probe described below. The 1.8 kilobase PCR product that could theoretically be generated from within flaB by pg3 priming does not appear.

Preparation of the Probe

Digestion of PCR-amplified *C. coli* VC167 DNA was performed with the restriction enzymes BglII and EcoRI and ligated to pUC18 vector DNA that had been digested with BamHI and EcoRI. Following transformation into DH5= cells, ampicillin-resistant, lacZ transformants were screened for the presence of a 273-bp insert into pUC18 by digesting them with XbaI and EcoRI. The purified fragment from one such clone, pBA273, was shown to hybridize to clones of the VC167 flagellin gene and when appropriately labeled (digoxigenin-dUTP from the Boehringer Mannheim Biochemicals [Indianapolis, Ind.] Genius kit introduced by random primers was used in these studies but other nucleotide labels, such as radiophosphate are also suitable) serves to detect a 450-base pair DNA product amplified by the primers pg50 and pg3.

Rabbit Experiments

Female New Zealand white rabbits (weight 0.9 to 1.1 kg; Hazelton Research Products, Denver, Pa.) were used. Animals were held for quarantine and acclimatization in a special holding area for at least 7 days before use. Experimental rabbits were fed bacterial suspensions as described by O. Pavlovskis, et al. (Infect. Immun. 59:2259– 2264, 1991). In brief, food was withheld 18–24 hr prior to oral administration of 15 ml of a bacterial suspension containing approximately $5 \times 10^9$ colony forming units with a feeding tube (2.7 mm [outer diameter] by 381 mm [length]) after neutralization of gastric acidity. Uninfected control rabbits were fed sterile broth. Rabbits were monitored by obtaining rectal swab specimens at approximately 48 hr postinfection. The swabs were transported to the laboratory in Cary Blair transport medium (Oxoid Ltd., Basingstoke, UK). The fecal material on the swabs was suspended in 0.5 ml of PBS to an optical density at 550 nm of approximately 0.35. Aliquots of this suspension were plated directly onto campylobacter blood agar plates (Remel, Lenexa, Kans.) and were incubated microaerobically for 48 hr at 37° C. Aliquots were also processed for PCR analysis by the method of Frankel et al. (ibid).

Human Stools

Human stool samples, which were obtained from Naval Medical Research Unit 3, Cairo, Egypt, were clinical specimens that had been submitted for routine bacteriological analysis from patients with acute diarrhea and that had been stored frozen for 3 to 12 months. Matched bacterial isolates from *C. jejuni*-positive stools were also obtained. Stools were extracted by a modification of the method of Frankel et al. (ibid) as developed by Branstrom et al. (Absts. 31st Intersci. Conf. Antimicrob. Agents Chemother. Abstract #1087, 1991).

Demonstration of Specificity

The primers pg50 and pg3 were initially evaluated for their ability to amplify a corresponding product from other strains of *C. coli* and from cultured *C. jejuni* strains. The primers generated the appropriately-sized fragment from DNA preparations from 3 other strains of *C. coli* and from 47 strains of *C. jejuni* isolated from a variety of geographical locations (Table 1). Hybridization studies with pGK213 as the probe indicated that the amplified material was flagellin specific. As summarized in Table 1, the primers failed to generate a detectable PCR product with DNA from 20 other strains of Campylobacter (8 species) or 103 other strains of enteric bacteria (7 genera, 13 species).

TABLE 1

Bacterial Strains Tested with Primer Set pg 3–pg 50

| Organism | Total No. of Strains Tested | Strain or Site of Isolation (No. of Strains) | Source[a] |
|---|---|---|---|
| *C. coli* | 4 | VC167 | Univ. Victoria |
| | | Canada | Univ. Victoria |
| *C. jejuni* | 47 | United States (2) | NMRI |
| | | Canada (6) | Univ. Victoria |
| | | Yemen (9) | NAMRU3 |
| | | Egypt (5) | NAMRU3 |
| | | West Africa (4) | NAMRU3 |
| | | Peru (4) | NAMRID |
| | | Panama (1) | NMRI |
| | | Mexico (1) | NMRI |
| | | Indonesia (15) | NAMRU2 |
| *C. lari* | 3 | D67 | CDC |
| | | D110 | CDC |
| | | D382 | CDC |
| *C. butzleri* | 1 | D2676 | CDC |
| *C. cryaerophila* (*Arcobacter cryoaerophilus*) cryaerophilus | 1 | D2792 (type strain) | CDC |
| *C. hyointestinalis* | 3 | D2189 | CDC |
| | | D2411 (porcine) | CDC |
| | | D1932 (type strain) | CDC |
| *C. upsaliensis* | 1 | D1673 | CDC |
| *C. fetus* subsp. intermedius | 3 | Australia | Univ. Victoria |
| *C. fetus* subsp. fetus | 7 | Canada | Univ. Victoria |
| *W. recta* (*C. recta*) | 1 | D2083 | CDC |
| *H. pylori* | 4 | Canada | Univ. Victoria |
| *V. cholerae* 01 | 11 | Kuwait or Iraq (7) | NAMRU3 |
| | | Senegal (1) | CVD |
| | | Kenya (2) | CVD |
| | | United States (1) | CVD |
| *V. cholerae* non-01 | 2 | United States (1) | CVD |
| | | Mexico (1) | CVD |
| *A. hydrophila* | 10 | Canada | Univ. Victoria |
| *A. sobria* | 1 | A412 | Univ. Victoria |
| *A. salmonicida* | 8 | Canada | Univ. Victoria |
| *E. coli* K-12 | 1 | DH5α | BRL |
| Enterotoxigenic *E. coli* | 52 | Egypt (30) | NAMRU3 |
| | | Saudi Arabia (18) | NAMRU3 |
| | | 263 (1) | CVD |
| | | Throop (1) | CVD |
| | | 286 (1) | CVD |
| | | SA53 (1) | CVD |
| *C. freundii* | 1 | United States | WRAIR |
| *S. dysenteriae* | 3 | 60R (1) | WRAIR |
| | | Egypt (2) | NAMRU3 |
| *S. flexneri* | 2 | Egypt (1) | NAMRU3 |
| | | 24570 (1) | WRAIR |
| *S. sonnei* | 8 | Saudi Arabia | NAMRU3 |
| *S. typhi* | 5 | 643 (1) | WRAIR |
| | | Egypt (4) | NAMRU3 |
| *S. typhimurium* | 1 | LT2 | WRAIR |
| *S. enteritidis* | 4 | Saudi Arabia | NAMRU3 |

[a]Sources of strains were as follows:
WRAIR - Walter Reed Army Institute of Research;
NMRI - Naval Medical Research Institute;
NAMRID - Naval Medical Research Institute Detachment, Lima, Peru;
NAMRU3 - Naval Medical Research Unit 3, Cairo, Egypt;

TABLE 1-continued

Bacterial Strains Tested with Primer Set pg 3–pg 50

| Organism | Total No. of Strains Tested | Strain or Site of Isolation (No. of Strains) | Source[a] |
|---|---|---|---|

NAMRU2 - Naval Medical Research Unit 2, Jakarta, Indonesia;
CDC - Center for Disease Control, Atlanta, GA;
CVD - Center for Vaccine Development, Baltimore, MD;
BRL - Bethesda Research Laboratories, Gaithersburg, MD;
and Univ. Victoria - University of Victoria strain collection.

Demonstration of Sensitivity

Using the digoxigenin-labeled pBA273 probe, serial dilutions of DNA extracted from cultured VC167 bacteria were subjected to PCR amplification using the pg3–pg50 primers, and the products were electrophoresed and transferred to a nylon membrane by Southern blotting (T. Maniatis, et al., ibid) and hybridized in 5$\times$SSC buffer (1$\times$SSC=0.015 M sodium citrate-0.15 M sodium chloride) for 16–24 hr at 60° C. with 230 ng of digoxigenin-labeled probe per 100 cm$^2$ of membrane. The results indicate that the PCR products generated with as little as 0.062 pg of DNA can be visualized on the agarose gel and that hybridization with the internal probe allows detection of a little as 0.0062 pg of DNA. Based on the genome size for Campylobacter spp. of 1,700 kilobase pairs, this corresponds to four or fewer bacteria.

In order to determine the sensitivity in stool samples, a normal human stool specimen is aliquoted into 1 g samples and seeded with serial dilutions of VC167 cells. Nucleic acid from each 0.5 g sample of seeded stool is extracted by the method of Branstrom et al. (ibid) into a final volume of 400 μL, and 5 μL of this is used in the PCR assay. The results of two separate experiments indicated that by hybridization analysis the assay could detect between 30–60 bacterial cells/5 μL sample used per PCR assay. The gel analysis was again 10-fold less sensitive than the hybridization.

In order to evaluate the feasibility of direct PCR detection of campylobacters in fecal material, rectal swabs were taken from 15 rabbits which were fed VC167 2 days prior to sampling, and from 15 control rabbits which had been fed sterile culture broth. Following transport to the laboratory in Cary Blair medium, aliquots of fecal material from each rabbit were re-suspended in phosphate buffered saline as described above. An aliquot from each sample was plated directly onto campylobacter blood agar and the plates were incubated microaerobically for 48 h. Another aliquot was processed for PCR using the extraction method of Frankel et al. (ibid), the products were dot blotted, and hybridized to the non-radioactively labelled internal probe from pBA273. The PCR assay detected *C. coli* in all 15 infected rabbits, although only 12/15 rabbits were positive by plating. No campylobacters were detected in the uninfected control rabbits by either PCR or plating.

Frozen human stool specimens (both culture-positive and culture-negative for *C. jejuni*) were obtained from field sites in Kuwait and Egypt, as well as the *C. jejuni* isolates from the positive stools. Stool samples were processed for PCR by the method of Branstrom et al. (ibid), and PCR products were electrophoresed and probed with pBA273. Four normal stools and four stools which were culture positive for Shigella sp. were tested; all 8 of these samples were negative in the PCR assay. Thirteen stools which were culture-positive for *C. jejuni* were examined. Of these 9/13 samples were positive by PCR as determined by agarose gel analysis. A fourth sample was determined to be positive only after hybridization to the probe. Three culture-positive stools from Egypt were also negative following hybridization. The strains which had been isolated from 2 of these stools were positive when examined directly by PCR analysis, but the isolate from the third stool was negative by the PCR assay.

Obviously, many modifications and variations of the present invention are possible in light of the above teachings. It is therefore to be understood that, within the scope of the appended claims, the invention may be practiced otherwise than as specifically described.

What we claim is:

1. An oligonucleotide 5'-ATGGGATTTCGTATTAAC-3'(SEQ ID No. 1).

2. An oligonucleotide 5'-GAACTTGAACCGATTTG-3'(SEQ ID No. 2).

3. A composition comprising a primer pair as used for amplifying DNA of the flagellin gene by polymerase chain reaction (PCR) from pathogenic strains *Campylobacter coli* and *Campylobacter jejuni* of Campylobacter wherein the primer pair consists of 5'-ATGGGATTTCGTATTAAC-3'(SEQ ID No. 1) and 5'-GAACTTGAACCGATTTG-3'(SEQ) ID No. 2).

4. The composition of claim 3 in combination with a labeled probe detecting sequences internal to the DNA amplified by the primer pair.

5. The composition of claim 4 wherein the probe is a segment of the Campylobacter flagell in gene.

6. A method of detecting the pathogenic strains *Campylobacter coli* and *Campylobacter jejuni* in stool specimens of patients with idiopathic diarrhea by PCR comprising amplifying the pathogenic strains with a primer pair consisting of 5'-ATGGGATTTCGTATTAAC-3'(SEQ ID No. 1) and 5'-GAACTTGAACCGATTTG- 3'(SEQ ID No. 2) and detecting the amplified DNA by observation of the amplified DNA fragment.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Campylobacter coli
        ( B ) STRAIN: VC167

( x ) PUBLICATION INFORMATION:
        ( A ) AUTHORS: Oyofo, Buhari A
            Thornton, Scott A
            Burr, Donald H.
            Trust, Trevor J
            Pavlovskis, Olgerts R
            Guerry, Patricia
        ( B ) TITLE: Specific Detection of Campylobacter jejuni
            and Campylobacter coli by Using Polymerase Chain
            Reaction
        ( C ) JOURNAL: J. Clin. Microbiol.
        ( D ) VOLUME: 30
        ( E ) ISSUE: 10
        ( F ) PAGES: 2613-2619
        ( G ) DATE: October-1992

( x i ) SEQUENCE DESCRIPTION: SEQ ID NO:1:

ATGGGATTTC GTATTAAC 18

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: Campylobacter coli
        ( B ) STRAIN: VC167

( x i ) SEQUENCE DESCRIPTION: SEQ ID NO:2:

GAACTTGAAC CGATTTG 17